United States Patent [19]
Slate et al.

[11] Patent Number: 5,911,703
[45] Date of Patent: Jun. 15, 1999

[54] TWO-STAGE FLUID MEDICAMENT JET INJECTOR

[75] Inventors: John B. Slate, San Diego; Michael W. Burk, San Marcos; Lanny A. Gorton, San Diego, all of Calif.

[73] Assignee: Avant Drug Delivery Systems, Inc., San Diego, Calif.

[21] Appl. No.: 08/861,968

[22] Filed: May 22, 1997

[51] Int. Cl.$^6$ .............................. A61M 5/30; A61M 5/20
[52] U.S. Cl. ............................................. 604/68; 604/135
[58] Field of Search ........................ 604/68–72, 131–136

[56] References Cited

U.S. PATENT DOCUMENTS

| | | |
|---|---|---|
| 2,101,140 | 12/1937 | Hege . |
| 3,605,745 | 9/1971 | Hodosh . |
| 3,640,277 | 2/1972 | Adelberg . |
| 3,690,318 | 9/1972 | Gorsuch . |
| 4,059,107 | 11/1977 | Iriguchi et al. . |
| 4,065,230 | 12/1977 | Gezari . |
| 4,150,672 | 4/1979 | Whitney et al. . |
| 4,403,609 | 9/1983 | Cohen . |
| 4,421,508 | 12/1983 | Cohen . |
| 4,437,859 | 3/1984 | Whitehouse et al. . |

(List continued on next page.)

OTHER PUBLICATIONS

Du Gas, B. W., Medications—Meeting Basic Needs, *Introduction to Patient Care,* Jan. 1, 1983, Published by W.B. Saunders, pp. 621–626.
King, E. M., *Illustrated Manual of Nursing Techniques,* Jan. 1, 1986, Published by J.B. Lippincott, pp. 496–500.
McConnell, Edwina A., RN, MS, The Subtle Art of Really Good Injections, *RN,* Feb., 1982, pp. 25–34.
National Institute of Health, Giving a Subcutaneous Injection, Published by U.S. Department of Health and Human Services, Jan. 1, 1995.
Rayman, G., Walker R., Day, J.O., Diabetic Medicine, *Patient Experience with a Jet Injector,* Jan. 1, 1989, pp. 6: 274–276.
Schneider, U., Birnbacker, R, Schober, E., Painfullness of Needle and Jet Injection in Children with Diabetes Mellitus, *European Journal of Pediatrics,* Jan. 1, 1994, pp. 153: 409–410.
Wolff, L., Weitzel, M.H., Fuerst, E.V., The Administration of Therapeutic Agents, *Fundamentals of Nursing,* Jan. 1, 1983,. Published by J.B. Lippincott, pp. 685–701.

*Primary Examiner*—Wynn Wood Coggins
*Assistant Examiner*—Michael J. Hayes
*Attorney, Agent, or Firm*—Nydegger & Associates

[57] ABSTRACT

A jet injector, and a method, for injecting fluid medicament into a patient in a two-stage process. During the first stage fluid is expelled from the injector under relatively high pressure, to create a hole through the skin of the patient. During the second stage, fluid is infused through the hole into the patient at a much lower pressure, and for a much longer period of time. The jet injector includes a syringe unit, and a drive mechanism which is selectively connectable with the syringe unit. Specifically, the drive mechanism includes two springs which are positioned to urge against a push rod as they elongate. When the drive mechanism is engaged with the syringe unit, the push rod is positioned longitudinally co-linear with a plunger in the chamber. When the springs are released, they push the push rod which, in turn, pushes the plunger, causing the fluid to be expelled through an injection tube connected to the chamber. The syringe unit also includes a suction compartment for pulling the skin against a syringe tip at the end of the injection tube. To prepare the injector, the chamber of the syringe unit is filled with a fluid medicament, the drive mechanism is cocked, and the syringe unit is engaged with the drive mechanism. A vacuum source is then connected in fluid communication with the suction compartment. The syringe tip and the opening to the suction compartment are then pressed against the skin, and the injector is activated.

16 Claims, 5 Drawing Sheets

U.S. PATENT DOCUMENTS

| | | |
|---|---|---|
| 4,518,385 | 5/1985 | Lindmayer et al. . |
| 4,623,332 | 11/1986 | Lindmayer et al. . |
| 4,680,027 | 7/1987 | Parsons et al. . |
| 4,722,728 | 2/1988 | Dixon . |
| 4,874,367 | 10/1989 | Edwards . |
| 5,024,656 | 6/1991 | Gasaway et al. . |
| 5,062,830 | 11/1991 | Dunlap . |
| 5,073,165 | 12/1991 | Edwards . |
| 5,074,843 | 12/1991 | Dalto et al. . |
| 5,116,313 | 5/1992 | McGregor . |
| 5,190,523 | 3/1993 | Lindmayer . |
| 5,312,335 | 5/1994 | McKinnon et al. . |
| 5,399,163 | 3/1995 | Peterson et al. . |
| 5,480,381 | 1/1996 | Weston . |
| 5,503,627 | 4/1996 | McKinnon et al. . |
| 5,503,628 | 4/1996 | Fetters et al. . |
| 5,505,697 | 4/1996 | McKinnon, Jr. et al. . |
| 5,520,639 | 5/1996 | Peterson et al. . |
| 5,599,302 | 2/1997 | Lilley et al. . |

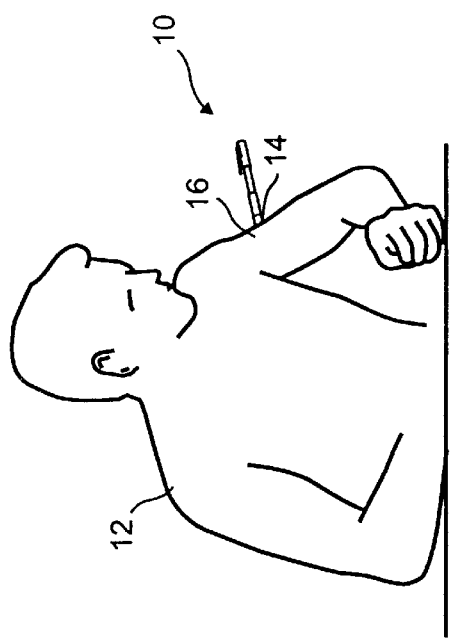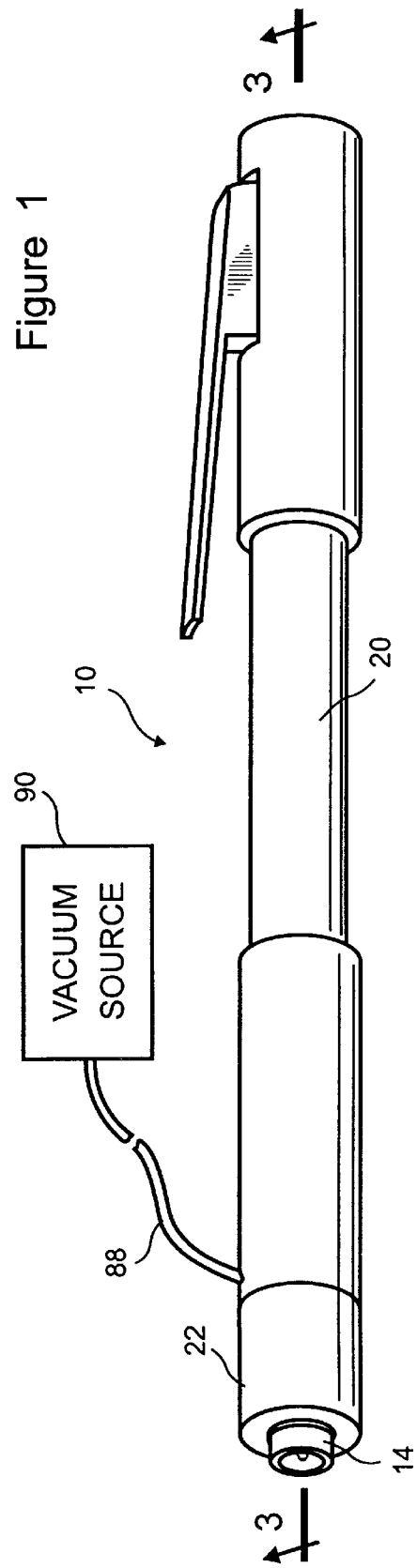

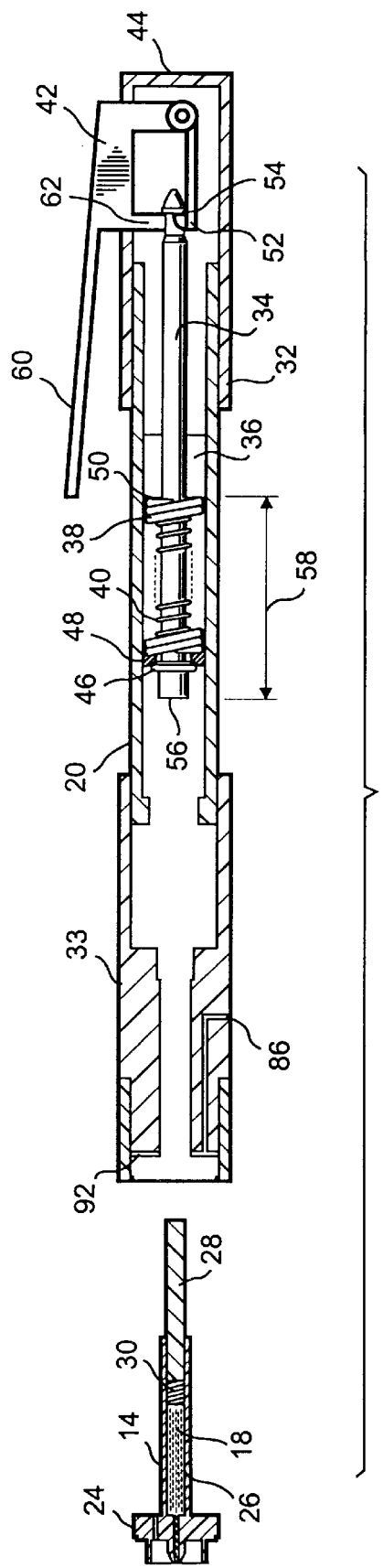
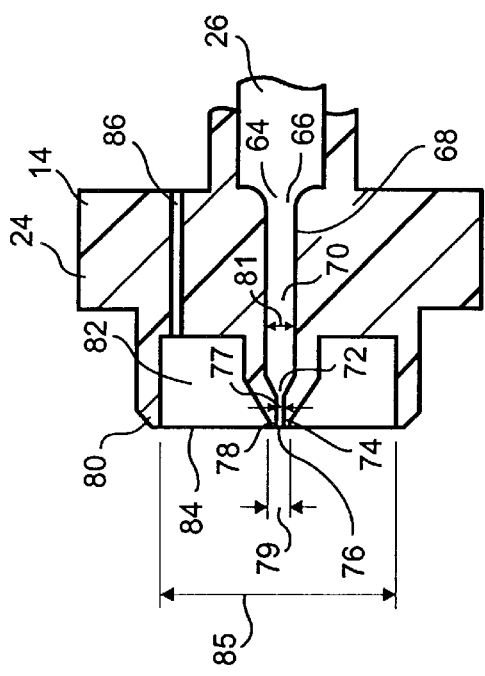
Figure 3
Figure 4

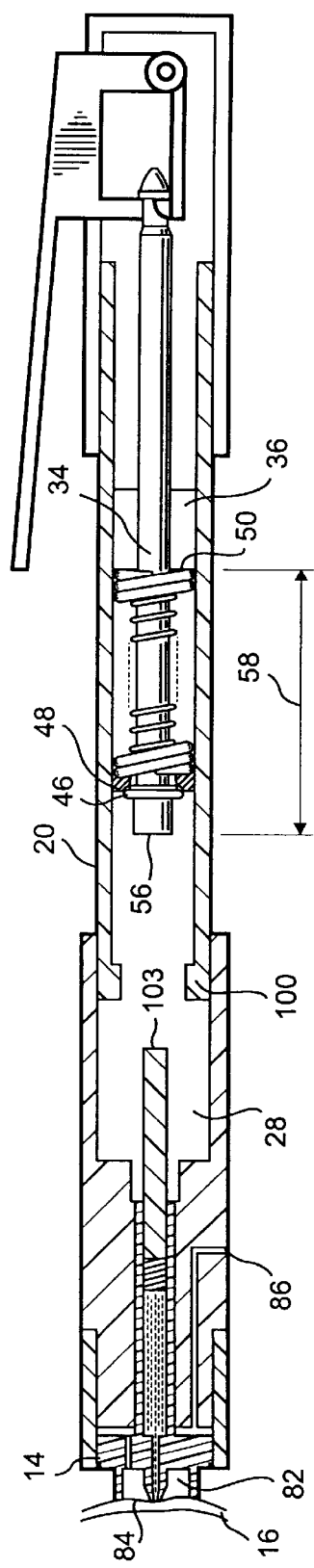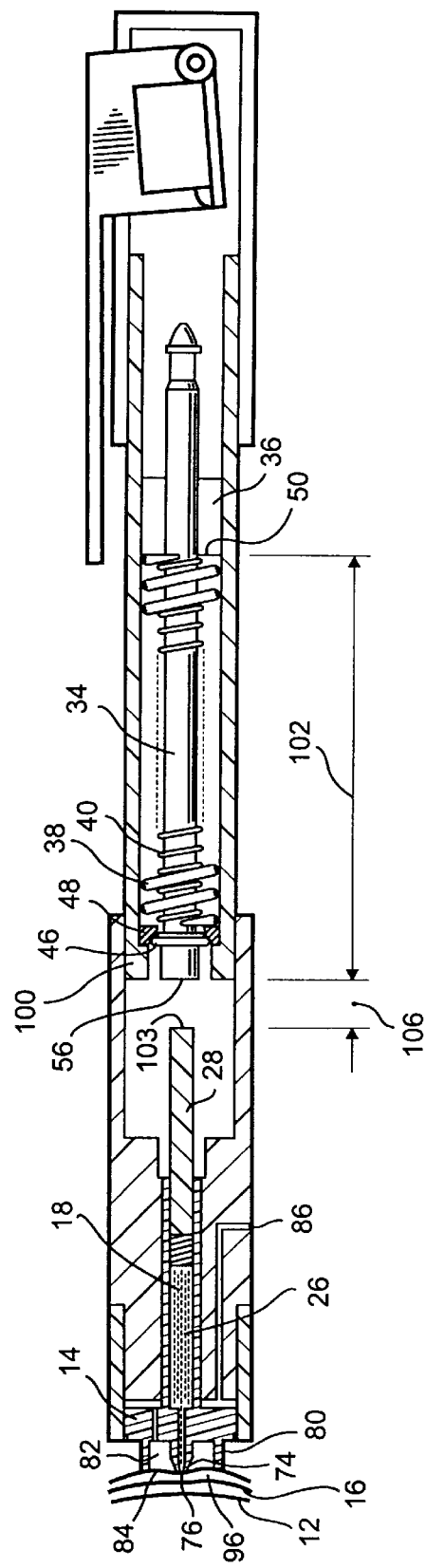
Figure 5
Figure 6

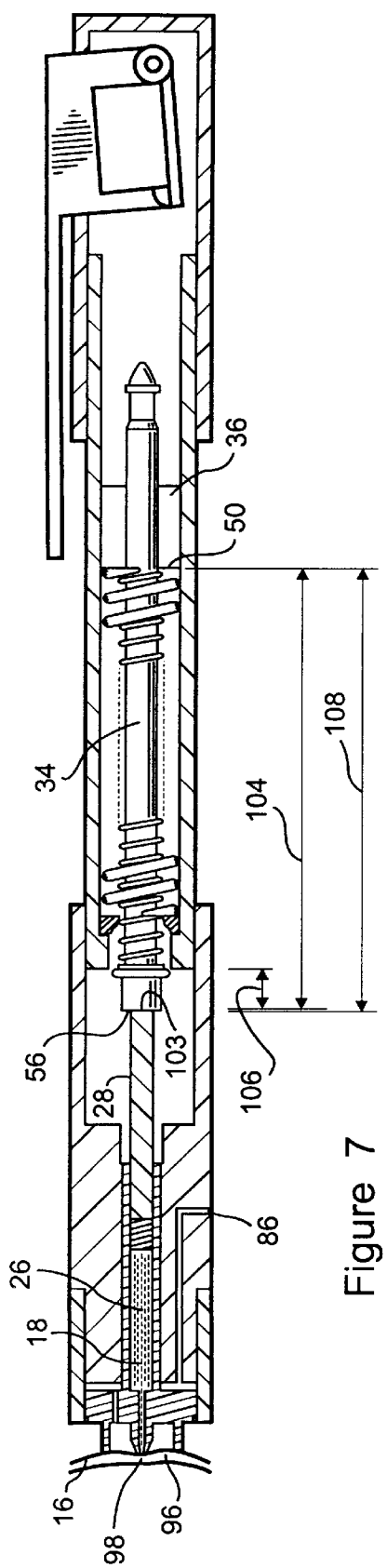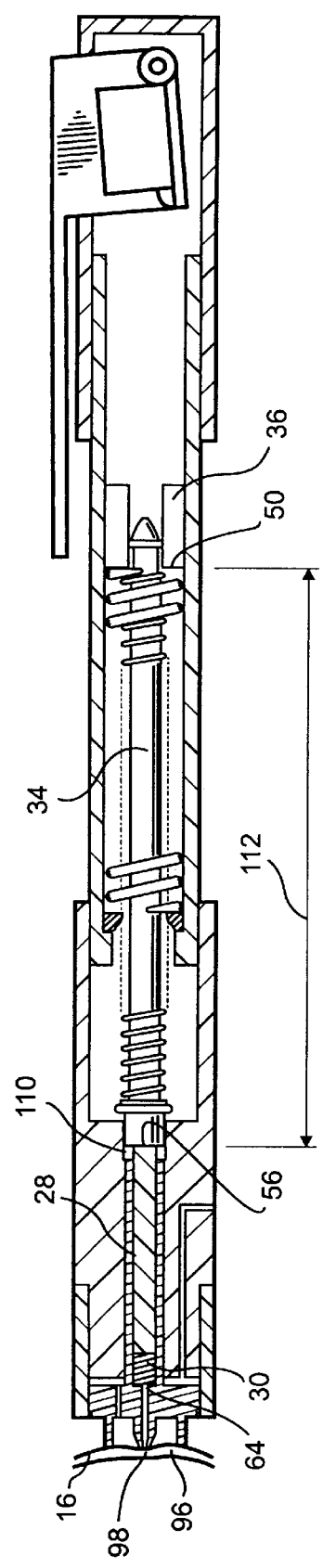

TWO-STAGE FLUID MEDICAMENT JET INJECTOR

FIELD OF THE INVENTION

The present invention pertains generally to medical devices and methods for using them. More particularly, the present invention pertains to devices and methods for administering medical injections. The present invention is particularly, but not exclusively, useful as a two-stage fluid medicament jet injector for automatically injecting a fluid medicament into a patient.

BACKGROUND OF THE INVENTION

Subcutaneous and intramuscular delivery of medicaments by injection are common in the medical arts. Examples of medical conditions that require frequent injections include diabetes, female infertility, AIDS, treatment of growth retardation in children, hepatitis, multiple sclerosis, migraine headaches, and allergic reactions. Traditionally, the medication for these and other ailments has been injected via a needle that punctures the skin of the patient. In many of these instances, the parenteral drugs are self-administered. For self-administered drugs it is particularly desirable that the injection be easily accomplished. Further, for circumstances requiring inoculations of a large number of persons, such as is often the case in the military services, it is also desirable that the inoculations be accomplished easily.

Despite the availability of fine gauge needles, many patients dislike needle injections due to pain, fear, and nervousness over needles. Additionally, practice has indicated there are serious risks related to needle injections. For example, blood-borne pathogens, such as HIV and hepatitis, can be transmitted to health care workers by accidental needle-sticks. Specific environments which have an exceptionally high risk of accidental needle-sticks include emergency rooms, county hospitals, and sites of mass immunizations. From these sources, hundreds of thousands of accidental needle-sticks are reported annually in the United States. The consequence is billions of dollars in annual costs due to the treatment of medical complications, testing and other related costs. Additionally, needle injections generate costs associated with the regulatorily required disposal of biohazardous sharps. For all of these reasons, there is a need for needle-free injection systems.

In efforts to minimize the fears, risks, and costs associated with needle injections, several types of needle-free jet injectors have been developed. Typically, such jet injectors expel all of their fluid medicament in a stream that is directed at a very high velocity. This high velocity stream accomplishes two tasks. First, due to its high velocity, the stream of fluid medicament is able to pierce a hole in the skin of the patient. Secondly, the stream injects the medicament through the hole into the patient.

Practice has indicated that existing needle-free jet injectors have several shortcomings. Most significantly, existing jet injectors have proven to be somewhat unsatisfactory due to side effects such as pain, bruising, and lacerations. These problems with existing injectors are largely caused by the high velocity at which the medicament is expelled into the patient throughout the injection process. Additionally, the strong contact that is required between the jet injector and the skin can contribute to bruising. Furthermore, movement of the injector during the injection process can cause lacerations. Also, with existing jet injectors, the high velocity at which the medicament is infused often causes undesirable painful enlargement of the hole in the skin of the patient during infusion of the medicament. In sum, practice has indicated that many patients desire a less painful injection than is currently available with existing jet injectors.

In addition to the difficulties noted above, the high velocity at which a medicament is infused by present jet injectors can also result in imprecise regulation of the depth of penetration of the medicament. For some patients this means the delivery of medicament may be directed into muscle tissue rather than into the subcutaneous tissue. If so, this may be undesirable if it leads to unpredictable drug absorption kinetics. Further, existing jet injectors have also proven to be inadequate due to incidents of incomplete drug delivery, and difficulty of use. In particular, incomplete drug delivery is often associated with uneven pressure between the skin and the injector during the injection.

Existing jet injectors with reusable syringes have additional shortcomings. For example, transmission of blood-borne pathogens is a risk associated with reusable syringes. Further, periodic disinfection of reusable syringes is an inconvenient necessity.

In light of the above, it is an object of the present invention to provide a needle-free medicament jet injector. Another object of the present invention is to provide a jet injector that administers an injection with minimal pain to the patient. Still another object of the present invention is to provide a jet injector that infuses the medicament into the patient at a lower velocity than existing jet injectors, so as to prevent harmful compression and damage to tissue, as well as to control the depth of the injection. It is still another object of the present invention to provide a jet injector with a stable skin to syringe interface to maintain consistent pressure between the skin and the syringe, and to prevent movement of the syringe relative to skin at the injection site during the injection. Yet another object of the present invention is to provide a jet injector with a disposable, replaceable, single-use syringe. Yet another object of the present invention is to provide a fluid medicament jet injector which is relatively simple to manufacture, is relatively easy to use, and is comparatively cost effective.

SUMMARY OF THE INVENTION

The two-stage jet injector of the present invention includes, in combination, a syringe unit, a drive mechanism for advancing the syringe plunger in a two-stage sequence, and a suction compartment which surrounds an injection tube of the syringe. In accordance with the present invention, these components allow the jet injector to consistently repeat a fluid medicament injection procedure which is efficient and which causes minimal pain to the recipient.

The syringe unit for the jet injector of the present invention is formed with a chamber for holding a fluid medicament. It also has a plunger which expels the fluid medicament from the syringe chamber as the plunger is advanced into the chamber. More specifically, as the plunger is advanced into the chamber, fluid medicament is expelled from an orifice in a syringe tip at the end of an elongated injection tube that extends in fluid communication from the chamber. The syringe tip itself is tapered to generally form a point around the orifice. Additionally, the syringe includes a hollow cylindrical shaped skirt which is attached to the chamber to extend therefrom and surround the injection tube. The extended end of the skirt then forms an opening surrounding the syringe tip. A suction compartment is thus established between the skirt and the injection tube, and this compartment will be closed whenever the opening to the suction compartment is covered. In order to create a partial vacuum in the suction compartment, a suction port is formed in the syringe unit, in fluid communication with the suction compartment. A vacuum source can then be selectively connected with the port to create a partial vacuum within the compartment. As indicated above, the syringe is selectively connectable with the drive mechanism.

For the present invention, the drive mechanism includes a push rod which is positioned longitudinally co-linear with the plunger of the syringe, when the syringe unit is operably connected to the drive mechanism. Accordingly, advancement of the plunger into the syringe chamber is caused by movement of the push rod. In accordance with the present invention, the push rod is driven by two separate springs, which are engaged with the push rod, and which are coaxially positioned around the push rod. Specifically, the first of the two coaxial springs is an impulse spring which is characterized by a relatively high spring constant and the fact that it is dimensioned to have a relatively short action distance. In comparison with the first spring, the second spring, a perfusion spring, has a lower spring constant and a longer action distance.

Initially, during acceleration of the push rod, both the impulse spring and the perfusion spring push on the push rod. However, it is primarily the force of the impulse spring that accelerates the push rod. The impulse spring expands until the impulse spring is restrained by a spring stop. After the impulse spring is stopped from expanding, the push rod continues moving through a coast distance, until the push rod collides with the plunger. As a result of this collision, the momentum of the push rod causes the plunger to accelerate very rapidly. This rapid advancement of the plunger is referred to as the impulse stage, and is the first of two stages of advancement of the plunger. The impulse stage is very brief, and lasts less than about five milliseconds (0.005 second). Due to the rapid advancement of the plunger during the impulse stage, the fluid is expelled through the injection tube and out the syringe tip under relatively high pressure. It happens that this high pressure creates a hole in the skin.

After the impulse stage, the perfusion spring continues to expand and push against the push rod. The result is a second stage, referred to as the perfusion stage. During the perfusion stage, the perfusion spring exerts a much smaller force against the push rod and plunger than the force which was exerted on the plunger during the impulse stage. Accordingly, fluid medicament is expelled from the syringe chamber at a much lower pressure and at a much lower rate than during the impulse stage. The duration of the perfusion stage is much longer than the duration of the impulse stage, and can last as long as five seconds, or longer. During the perfusion stage, fluid medicament is allowed to slowly infiltrate into tissue in the subcutaneous pocket.

In the operation of the present invention, the two-stage jet injector is first prepared for injection. One step in this preparation is the cocking of the drive mechanism. When the drive mechanism is cocked, both of the coaxial springs are compressed to thereby store the potential energy that is necessary for subsequent operation of the jet injector. Further, the cocking operation also positions the push rod against both of the compressed springs. As so positioned, the push rod is ultimately able to receive energy from the springs as they elongate when the jet injector is activated. Another step in preparing the jet injector requires the engagement of the drive mechanism with a syringe that is filled, or is to be filled, with fluid medicament. As stated above, this engagement positions the push rod longitudinally co-linear with the plunger. Finally, a vacuum source is connected in fluid communication with the suction compartment of the syringe. The jet injector is thus prepared for giving an injection to a patient.

To give an injection with the jet injector of the present invention, the syringe tip is placed against a point on the patient's body selected by the operator. Because the skin around this point covers the opening to the suction compartment around the syringe tip, the suction compartment becomes enclosed. Consequently, with the syringe tip in place against the patient's body, a partial vacuum is created in the syringe compartment by the vacuum source. This partial vacuum causes the skin across the opening to be drawn into the suction compartment, thereby establishing a subcutaneous pocket around the syringe tip. The jet injector is then activated to inject the fluid medicament into the patient in the two-stage process as described above.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a generalized view of the two-stage fluid medicament jet injector of the present invention in its operative environment;

FIG. 2 is a perspective view of the two-stage fluid medicament jet injector of the present invention showing the syringe unit engaged with the drive mechanism;

FIG. 3 is a cross-sectional view of the syringe unit of the present invention as would be seen along the line 3—3 in FIG. 2, but with the syringe unit separated from the drive mechanism;

FIG. 4 is a cross-sectional view of the head of the syringe unit of the present invention as would be seen along the line 3—3 in FIG. 2;

FIG. 5 is a cross-sectional view of the two-stage fluid medicament jet injector of the present invention as would be seen along the line 3—3 in FIG. 2, with the drive mechanism cocked, and the skin area pressed against the opening to the suction compartment prior to operation of the injector;

FIG. 6 is a cross-sectional view of the injector as shown in FIG. 5, with the impulse spring fully extended after initial acceleration of the push rod;

FIG. 7 is a cross-sectional view of the jet injector as shown in FIG. 5, during the impulse contact of the push rod against the syringe plunger.

FIG. 8 is a cross-sectional view of the jet injector as shown in FIG. 5, after delivery of the medicament has been completed.

DESCRIPTION OF THE PREFERRED EMBODIMENT

Figure 9:
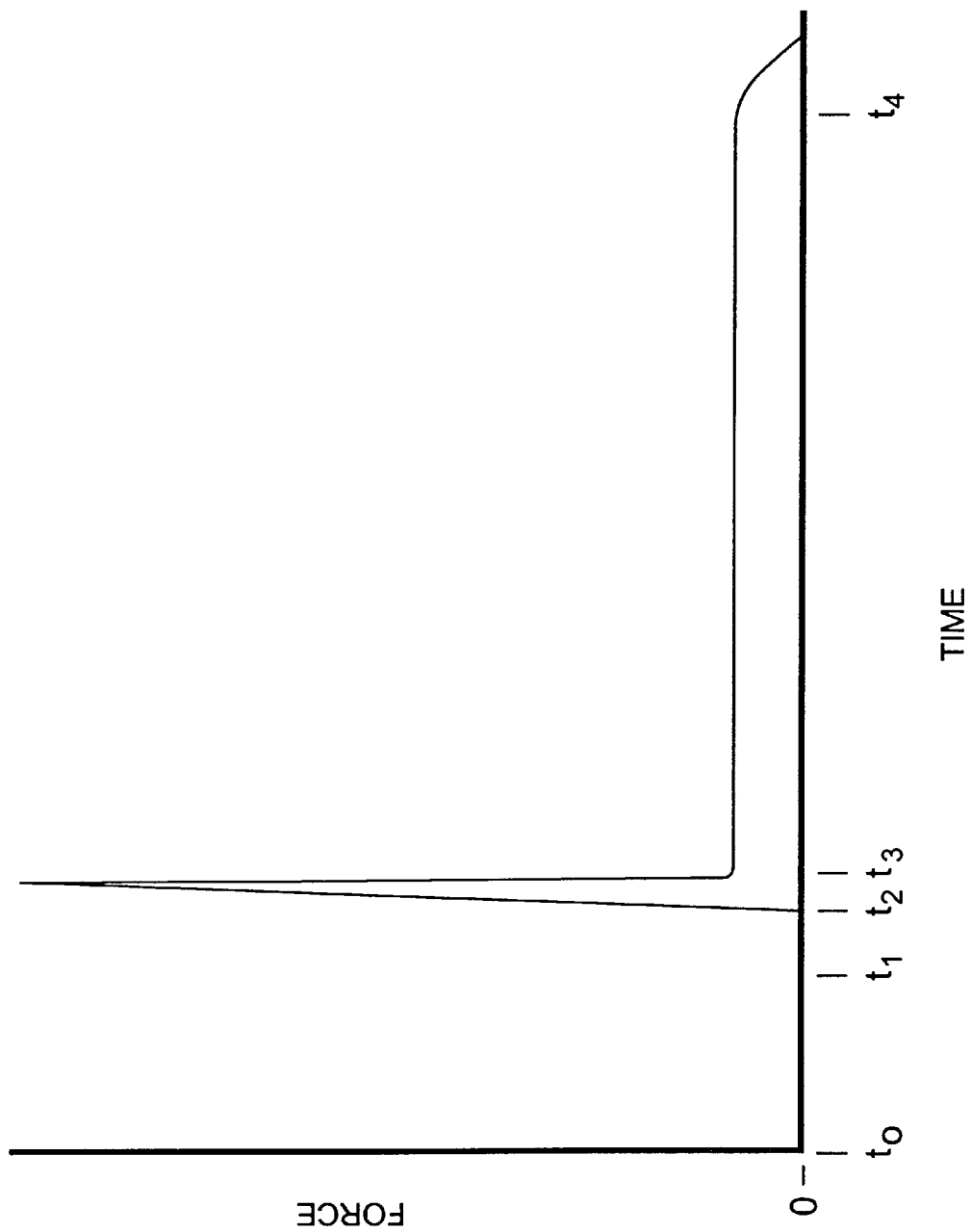
FIG. 9 is a graph depicting the force with which the fluid medicament is expelled from the jet injector, plotted as a function of time.

Referring initially to FIG. 1, a two-stage fluid medicament jet injector, also referred to as the apparatus, in accordance with the present invention is shown in its operative environment and is generally designated 10. As intended for the present invention, in order to administer an injection to a patient 12, the injector 10 is simply positioned against the patient 12 much like an ordinary manually operated syringe.

Specifically, a syringe unit 14 of the jet injector 10 is pressed against a skin area 16 of the patient 12. Unlike an ordinary manually operated syringe, however, after being activated the injector 10 of the present invention automatically infuses a fluid medicament 18 into the patient 12.

Referring to FIG. 2, it can be seen that the jet injector 10 includes the syringe unit 14, and a drive mechanism 20. The syringe unit 14 is detachable from the drive mechanism 20, and can be secured to the drive mechanism 20 with a connecting hub 22 of a type well known in the pertinent art such as threads. It will be further appreciated by the skilled artisan that the detachability of the syringe unit 14 facilitates one-time use of the syringe unit 14 and repeated usage of the drive mechanism 20. Such one-time use greatly reduces the risk of transmission of blood borne pathogens, and eliminates the need to disinfect the syringe unit 14 after administration of an injection.

Referring now to FIG. 3, the syringe unit 14 is shown separated from the drive mechanism 20. It can be seen that the syringe unit 14 includes a head 24, a chamber 26 for holding the fluid medicament 18, and a plunger 28. The plunger 28 is slidably disposed in the chamber 26. As will be appreciated by the skilled artisan, during administration of an injection, the plunger 28 is advanced into the chamber 26 to expel fluid medicament 18 from the chamber 26. The plunger 28 has a seal 30, to prevent the fluid medicament 18 from escaping around the outside of the plunger 28, so as to maintain the pressure on the fluid medicament 18 in the chamber 26. The seal 30 can be an "o-ring" made of rubber or other elastic material, or the seal 30 may be molded as an integral part of the plunger 28.

Still referring to FIG. 3, the drive mechanism 20 can be seen to include a housing 32, which includes a syringe holder 33. A push rod 34, which is slidably disposed on the housing 32, can also be seen. Guide 36 guides the movement of the push rod 34, so that the longitudinal axis of the push rod 34 remains parallel to the longitudinal axis of the drive mechanism 20. The drive mechanism 20 can be seen to also include an impulse spring 38 and a perfusion spring 40. Both the impulse spring 38 and the perfusion spring 40 are positioned between the housing 32 and the push rod 34. The springs are also located coaxially around the push rod 34, with one end of the springs abutting against the guide 36.

The drive mechanism 20 also includes a trigger 42 which is hingably mounted on the housing 32. When the push rod 34 is pushed towards the back wall 44 of the housing 32, a collar 46 of the push rod 34 pushes against the perfusion spring 40, and the collar 46 also pushes against a sliding guide ring 48 which abuts an end of the impulse spring 38. The sliding guide ring 48 is formed so that it surrounds but does not contact the perfusion spring 40. When the push rod 34 is pushed towards the back wall 44 of the housing 32, the perfusion spring 40 is compressed between the collar 46 and a face 50 of the guide 36, and the impulse spring 38 is compressed between the sliding guide ring 48 and the face 50 of the guide 36. At this point it is noted that a middle portion of the impulse spring 38 has been removed from the Figure for clarity. When the springs 38, 40 are compressed, a latch 52, which is hingably connected to the housing 32, can be engaged with a catch 54 of the push rod 34 to hold the push rod 34 in a cocked configuration. For purposes of disclosure, when the push rod 34 is in this cocked configuration, it will be discussed as being in a first position, with an end 56 of the push rod 34 located a first distance 58 from the face 50 of the guide 36.

Still referring to FIG. 3, it can be seen that the drive mechanism 20 also includes a trigger arm 60 which is connected to the trigger 42. The trigger arm 60 is used to release the push rod 34 from the trigger 42. Specifically, when the trigger arm 60 is moved towards the housing 32, a cross member 62 of the trigger arm 60 pushes the latch 52 of the trigger 42 out of contact with the catch 54 of the push rod 34. This frees the push rod 34 to be moved by the force of the compressed springs 38, 40. The drive mechanism 20 can be seen in a cocked configuration in FIGS. 3 and 5, and with the push rod 34 released from the trigger 42 in FIGS. 6, 7 and 8.

Referring now to FIG. 4, details of the head 24 of the syringe unit 14 can be seen. It can be seen that the chamber 26 is formed with an aperture 64, and that a first end 66 of an injection tube 68 is connected in fluid communication with the aperture 64. A lumen 70 in the injection tube 68 extends between the first end 66 and a second end 72 of the injection tube 68 to establish fluid communication between the chamber 26 and the second end 72 of the injection tube 68. The syringe unit 14 is also formed with a syringe tip 74 having an orifice 76, which is in fluid communication with the second end 72 of the injection tube 68. The orifice 76 is circular, and the orifice 76 has a diameter 77 that is smaller than the diameter 81 of the injection tube 68. The diameter 77 of the orifice 76 can range from about three thousands of an inch (0.003 inch) to about fifteen thousandths of an inch (0.015 inch), and is preferably about eight thousandths of an inch (0.008 inch). It will be appreciated by the skilled artisan that orifice 76 shapes other than circular can also be used. It will also be appreciated that when the plunger 28 pushes the fluid medicament 18 into the injection tube 68, the comparatively smaller diameter of the orifice 76 greatly increases the pressure with which the fluid medicament 18 is expelled from the syringe tip 74. Additionally, it can be seen that the syringe tip 74 has a crown 78, and that the syringe tip 74 is tapered, to reduce a outer diameter 79 of the crown 78. The diameter 79 of the crown 78 can range from about thirty thousandths of an inch (0.030 inch) to about forty-five thousandths of an inch (0.045 inch). It will be appreciated by the skilled artisan that tapering the syringe tip 74 and thereby reducing the diameter 79 of the crown 78 facilitates maintaining a tight interface between the orifice 76 and the skin area 16, when the skin area 16 is pulled against the syringe tip 74, without having to push the syringe tip 74 firmly into the skin area 16, which can cause both pain and tissue damage.

For the present invention it is important to note that the syringe unit 14 is also formed with a generally cylindrical shaped skirt 80 which encircles the syringe tip 74 and which is generally coaxial therewith. Specifically, the skirt 80 defines a potential suction compartment 82 in the syringe unit 14. Further, the suction compartment 82 has an opening 84 which encircles the syringe tip 74 (or the aperture 64 in an alternative embodiment). A diameter 85 of the opening 84 to the suction compartment 82 can range from about four tenths of an inch (0.4 inch) to about seven tenths of an inch (0.7 inch), and is preferably about one-half of an inch (0.5 inch). In order to establish a suction in the suction compartment 82, a suction port 86 is formed in the head 24 for connecting a suction connector 88 and vacuum source 90 (shown in FIG. 2) in fluid communication with the suction compartment 82. In this embodiment, the suction port 86 can be seen in FIG. 3 to continue through the drive mechanism 20, for the suction connector 88 to connect with the suction port 86 at the drive mechanism 20. Vacuum seal 92 can also be seen. Alternatively, the suction port 86 can be contained completely within the head 24 of the syringe unit 14, with the suction connector 88 connecting with the suction port 86, at the syringe unit 14, or at the connecting hub 22. It will be appreciated that a partial vacuum is created in the suction compartment 82 when the vacuum source 90 is connected in fluid communication with the suction compartment 82, and the opening 84 to the suction compartment 82 is covered. It will be appreciated by the skilled artisan that the vacuum allows for the creation of a seal between the skin area 16 and the syringe tip 74 without having to compress the skin area 16 and underlying tissue, which is associated with pain and tissue damage. It will be further appreciated that the tapered syringe tip 74 allows a tight seal between the syringe tip 74 and the skin area 16 to be maintained with a lesser vacuum than would be required if the tip 74 were not tapered. It will be appreciated that the moderate vacuum pressure required avoids causing bruising or ruptures cutaneous blood vessels and minimizes patient discomfort.

Referring now to FIG. 5, the syringe unit 14 is shown engaged with the drive mechanism 20. The push rod 34 is shown in the first position, with the drive mechanism 20 in a cocked configuration. It can be seen that when the syringe unit 14 is engaged with the drive mechanism 20, the push rod 34 is aligned longitudinally co-linear with the plunger 28.

In FIG. 5 the opening 84 in the suction compartment 82 of the syringe unit 14 is shown pressed against the skin area 16 of the patient 12, prior to establishing fluid communication between the vacuum source 90 and the suction compartment 82. This configuration can be compared to the configuration shown in FIG. 6, in which the vacuum source 90 has been connected in fluid communication with the suction compartment 82.

Referring to FIG. 6, the skirt 80 and the opening 84 in the suction compartment 82 of the syringe unit 14 are shown pressed against the skin area 16 of the patient 12, after fluid communication has been established between the vacuum source 90 and the suction compartment 82. It can be seen that the resulting partial vacuum in the suction compartment 82 causes the skin area 16 of the patient 12 to be drawn into the suction compartment 82. The drawing of the skin area 16 in to the suction compartment 82 creates a subcutaneous pocket 96, and also results in the skin area 16 being pulled against the orifice 76 of the syringe tip 74. It will be appreciated by the skilled artisan that the resulting seal between the skin area 16 and the syringe tip 74 enables the fluid medicament 18 to be slowly perfused into the subcutaneous pocket 96 without leakage. It will also be appreciated that the subcutaneous pocket 96 facilitates infusion of the fluid medicament 18 into the patient 12 by creating a space for the fluid medicament 18 to infuse into. It will also be appreciated by the skilled artisan that drawing the skin area 16 into the suction compartment 82 prevents movement of the syringe unit 14 relative to the skin area 16. This stable interface between the syringe unit 14 and the skin area 16 prevents lacerations and tissue damage that can be caused by movement of the syringe unit 14. It will be further appreciated by the skilled artisan that the stable interface between the syringe unit 14 and the skin area 16, together with adequate pressure during delivery, helps to ensure complete medication delivery. It will be still further appreciated by the skilled artisan that pulling the skin area 16 against the orifice 76 of the syringe tip 74 facilitates creation of a hole 98 through the skin area 16 during administration of the injection. The hole 98 is depicted in FIGS. 7 and 8.

In order to minimize the size of the hole 98 and to gently infuse the fluid medicament 18 into the patient 12, the jet injector 10 expels the fluid medicament 18 in two stages. Delivery of the medicament 18 in two stages is facilitated by having different characteristics for the springs 38, 40. Accordingly, the impulse spring 38 is formed with a higher spring constant than the perfusion spring 40. This means that when the impulse spring 38 and the perfusion spring 40 are both compressed, the impulse spring 38 pushes against push rod 34 with a greater force than the perfusion spring 40. The impulse spring 38 also has a shorter action distance than the perfusion spring 40. Additionally, the expansion of the impulse spring 38 is limited by a stop 100. Consequently, when the impulse spring 38 and the perfusion spring 40 are both released from a compressed state, the impulse spring 38 expands and pushes the push rod 34 a shorter distance than the perfusion spring 40.

When the push rod 34 is released from the cocked configuration shown in FIG. 5, both the impulse spring 38 and the perfusion spring 40 accelerate the push rod 34 and move the push rod 34 from the first position shown in FIG. 5, to a second position shown in FIG. 6. However, because the impulse spring 38 pushes with a much stronger force than the perfusion spring 40, the impulse spring 38 primarily moves and accelerates the push rod 34 between the first and second positions, which is also referred to as the acceleration zone. It will be appreciated by the skilled artisan that other sources of motive force, such as a motor or solenoid, can be used to accelerate the push rod 34. When the springs 38, 40 expand, the perfusion spring 40 pushes against the collar 46 of the push rod 34, and the impulse spring 38 pushes against the sliding guide ring 48, which pushes the collar 46 of the push rod 34. The expansion of the impulse spring 34 is stopped when the sliding guide ring 48 hits the stop 100. When the sliding guide ring 48 reaches the stop 100, the push rod 34 is in the second position. When the push rod 34 is in the second position, as shown in FIG. 6, the end 56 of the push rod 34 is a second distance 102 from the face 50 of the guide 36.

Due to the momentum of the push rod 34, and to a lesser extent due to the continued pushing by the perfusion spring 40, the push rod 34 continues moving towards the plunger 28, after the expansion of the impulse spring 38 has been stopped. The end 56 of the push rod 34 eventually collides with a base 103 of the plunger 28, creating a first force on the fluid medicament 18. When the end 56 of the push rod 34 pushes the base 103 of the plunger 28, the plunger 28 advances into the chamber 26, causing the fluid medicament 18 to be expelled from the orifice 76.

As a result of the collision, the momentum of the push rod 34 is transferred to the plunger 28. The collision causes a high velocity, short duration, impulse function of the fluid medicament 18 to be expelled from the orifice 76, sufficient to create the hole 98 through the skin area 16. This high velocity jet of a minute amount of the fluid medicament 18 punctures the skin area 16 of the patient 12, thereby creating the hole 98 through the skin area 16 of the patient 12. It will be appreciated by the skilled artisan that the hole 98 created by the brief, initial jet pressure is comparable to that of a fine gauge needle. This small hole 98 causes less pain than current injectors, which continue to enlarge the hole 98 as a result of their rapid delivery of the remainder of the fluid medicament 18. It will also be appreciated by the skilled artisan that the depth of the hole 98 is a function of the force of the jet of the fluid medicament 18. It will be further appreciated that the force of the jet of the fluid medicament 18 is a function of the characteristics of the springs 38, 40, the mass of the push rod 34, the distance that the impulse spring 38 is allowed to expand and thereby accelerate the push rod 34, the cross-sectional area of the chamber 26, the cross-sectional area of the orifice 76, and the elastic properties of the plunger 28, among other factors. In the preferred embodiment the fluid medicament 18 is delivered to the subcutaneous tissue and not into muscle tissue, resulting in consistent bioavailabilty and improved drug absorption predictability. In alternative embodiments, the depth of penetration of the fluid medicament 18 can be altered by adjusting the above-factors. Therefore, the depth of penetration can be extended if it is desired to inject the fluid medicament 18 into muscle tissue.

When the end 56 of the push rod 34 first contacts the base 103 of the plunger 28, the push rod is in a third position, in which the end 56 of the push rod 34 is a third distance 104 from the face 50 of the guide 36. The third distance 104 is shown in FIG. 7 (however, the push rod 34 is shown in a fourth position in FIG. 7). The distance that the end 56 of the push rod 34 travels between the second position and the third position, is referred to as the push rod coast zone distance 106, which is shown in FIGS. 6 and 7. It will be appreciated that the third distance 104, and the push rod coast zone distance 106, are functions of the amount of fluid medicament 18 in the chamber 26, which determines the location of the base 103 of the plunger 28. In less than about five milliseconds (0.005 second) after the end 56 of the push rod 34 contacts the base 103 of the plunger 28, the initial high velocity jet of the fluid medicament 18 is expelled from the orifice 76, and the hole 98 is created in the skin area 16. Immediately after the initial high velocity jet of the fluid medicament 18 has been expelled, the push rod 34 is in a fourth position, shown in FIG. 7, in which the end 56 of the push rod 34 is a fourth distance 108 from the face 50 of the guide 36. The advancement of the end 56 of the push rod 34 from the third distance 104 to the fourth distance 108, during which the high velocity jet of fluid medicament 18 is expelled, is referred to as the impulse stage, the first stage of the two-stage injection. It will be appreciated that the third position and the fourth position of the push rod 34 are nearly identical, because the push rod 34 advances only very slightly while the impulse of fluid medicament 18 is expelled from the orifice 76.

After the initial impulse jet of fluid medicament 18 has been expelled from the orifice 76, the perfusion spring 40 continues pushing the push rod 34, creating a second force on the fluid medicament 18. When the perfusion spring 40 alone pushes on the push rod 34, the acceleration of the push rod 34 is small in comparison to the acceleration when the impulse spring 38 was also pushing on the push rod 34, due to the lower spring constant of the perfusion spring 40. It will be appreciated by the skilled artisan that other sources of motive force, such as a motor or solenoid, can be used instead of the perfusion spring 40 to continue the movement of the push rod 34.

The push rod 34 rod is pushed by the perfusion spring 40 from the fourth position shown in FIG. 7, to a fifth position shown in FIG. 8. The push rod 34 stops moving when the end 56 of the push rod 34 rests against a limiter 110, which prevents the push rod 34 from moving any further. When the end 56 of the push rod 34 reaches the limiter 110, the seal 30 of the plunger 28 simultaneously reaches the aperture 64 of the chamber 26, thereby completing the expellation of the fluid medicament 18. When the push rod 34 is in the fifth position shown in FIG. 8, the end 56 of the push rod 34 is a fifth distance 112 from the face 50 of the guide 36. The advancement of the end 56 of the push rod 34 from the fourth distance 108 to the fifth distance 112, during which the fluid medicament 18 is slowly infused into the skin area 16 of the patient 12, is referred to as the perfusion stage, the second stage of the two-stage injection. Preferably, the perfusion stage lasts at least about two seconds (2 seconds). It will be appreciated that the duration of the perfusion stage is a function of the quantity of fluid medicament 18 in the chamber 26, among other factors.

The two stages during which the fluid medicament 18 is expelled from the orifice 76 of the injector 10 are illustrated in terms of force and time in FIG. 9. FIG. 9 is a graph depicting the force with which the fluid medicament 18 is expelled from the orifice 76 on the y-axis, plotted against time on the x-axis. The injection process begins when the trigger arm 60 is pressed at time $t_0$ shown in FIG. 9. FIG. 5 shows the injector 10 as the injector 10 is configured immediately prior to time $t_0$. Between time $t_0$ and time $t_1$, the push rod 34 is accelerated by the impulse spring 38. FIG. 6 shows the injector 10 at time $t_1$, which is when the impulse spring 38 contacts the stop 100. After the impulse spring 38 contacts the stop 100, the push rod 34 travels across the coast zone distance 106, which is shown in FIGS. 6 and 7. After the push rod 34 travels across the coast zone distance 106, the end 56 of the push rod 34 collides with the base 103 of the plunger 28 at time $t_2$, shown in FIG. 9.

Fluid medicament 18 begins to be expelled from the orifice 76 at time $t_2$, which is the beginning of the impulse stage. The impulse stage continues until time $t_3$, which is when substantially all of the momentum imparted to the push rod 34 by the impulse spring 38 has been transferred to the plunger 28. As can be seen in FIG. 9, due to the impulse of momentum imparted to the plunger during the impulse stage, the fluid 18 is expelled with a relatively large force during the relatively brief impulse stage. This force creates the hole 98 in the skin area 16 of the patient 12, shown in FIG. 7.

The time $t_3$ marks the end of the impulse stage and the beginning of the perfusion stage, which lasts from time $t_3$ to time $t_4$. During the perfusion stage the push rod 34 is pushed by the perfusion spring 40, causing the fluid 18 to be infused into the patient 12 through the hole 98 in the skin area 16. The injector 10 is shown at the beginning of the perfusion stage at time $t_3$ in FIG. 7, and at the end of the perfusion stage at time $t_4$ in FIG. 8. In FIG. 9 it can be seen that the perfusion stage has a much longer duration than the impulse stage, and that the fluid 18 is expelled with much less force during the perfusion stage than during the impulse stage.

As mentioned above, the impulse stage lasts less than about five milliseconds (0.005 second), during which the fluid medicament 18 is rapidly expelled from the orifice 76. In contrast, during the perfusion stage, the fluid medicament 18 is gradually infused through the hole 98 through the skin area 16 into the subcutaneous pocket 96 of the patient 12. The perfusion stage typically lasts from about two seconds (2 seconds) to about five seconds (5 seconds), depending on the volume of the medicament 18, the pushing force of the perfusion spring 40, and the characteristics of the skin area 16, among other factors. It will be appreciated by the skilled artisan that delivering the fluid medicament 18 slowly over several seconds simulates an ideal subcutaneous injection by a nurse trained to minimize pain.

OPERATION

To administer an injection with the two-stage fluid medicament jet injector 10 of the present invention, first the drive mechanism 20 is cocked. The cocking is accomplished by pushing the collar 46 of the push rod 34 against the sliding guide ring 48, and the perfusion spring 40. This causes the springs 38, 40 to be compressed between the collar 46 and the face 50 of the guide 36. The latch 52 of the trigger 42 is then latched on the catch 54 of the push rod 34. The latch 52 thereby holds the push rod 34 in the first position with the springs 38, 40 compressed. The fluid medicament 18 is then placed in the chamber 26 of the syringe unit 14, preferably by utilizing a single-use vial adapter. Next, the syringe unit 14 is engaged with the drive mechanism 20. The suction connector 88 is then connected to the vacuum source 90 and to the suction port 86 in the jet injector 10. Fluid communication is thereby established between the vacuum source 90 and the suction compartment 82. The orifice 76 of the syringe tip 74 (or in an alternative embodiment, the aperture 64 of the chamber 26), and the opening 84 to the suction compartment 82, and are then pressed against the skin area 16 of the patient 12, thereby covering the opening 84 to the suction compartment 82. Covering the opening 84 to the suction compartment 82 with the skin area 16 of the patient 12 causes a partial vacuum to be created in the suction compartment 82. The partial vacuum draws the skin area 16 into the suction compartment 82, thereby creating the subcutaneous pocket 96, and thereby also pulling the skin area 16 against the orifice 76 of the syringe tip 74 (or in an alternative embodiment, against the aperture 64 of the chamber 26). The jet injector 10 having been prepared for the injection and properly positioned against the skin area 16 of the patient 12, the trigger arm 60 is then pushed toward the housing 32. This causes the push rod 34 to be released from the trigger 42, which results in the fluid medicament 18 being expelled from the jet injector 10 and into the patient 12 in the two-stage process.

It will be appreciated that the apparatus described herein can be employed for purposes other than administering injections. For example, the initial controlled pulse can be used to generate holes in the skin for allergen reaction testing. Another possible alternative use is using the initial controlled pulse to generate holes in the skin for tattooing, which would limit the risk of blood borne diseases and would be much less painful than traditional tattooing methods.

While the particular two-stage fluid medicament jet injector, and the method for injecting a fluid medicament, as herein shown and disclosed in detail are fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for injecting a fluid medicament through a skin area into a patient, which comprises:
    a chamber for containing the fluid medicament, said chamber having an aperture;
    a drive mechanism for selectively exerting forces on the fluid in said chamber to sequentially expel the fluid through said aperture in two stages, said stages being an impulse stage characterized by a first force on the fluid wherein fluid punctures the skin area of the patient to create a hole through the skin, and a perfusion stage characterized by a second force on the fluid wherein fluid is injected into the patient through the hole, said second force being less than said first force;
    an injection tube formed with a lumen and having a first end and a second end, said first end of said injection tube being attached to said chamber to extend said injection tube therefrom with said lumen in fluid communication with said chamber through said aperture;
    a skirt attached to said chamber and extending therefrom to surround said injection tube and establish a suction compartment therebetween, said skirt being distanced from said second end of said injection tube to establish an opening into said suction compartment; and a vacuum source in fluid communication with said suction compartment for creating a subcutaneous pocket in said suction compartment for infusion of said fluid medicament.

2. An apparatus as recited in claim 1 wherein said impulse stage has a duration of less than about 0.005 second, and wherein said perfusion stage has a duration of at least about 2 seconds.

3. An apparatus as recited in claim 1 wherein said apparatus includes a syringe unit comprising said chamber, said injection tube and said skirt, and wherein said syringe unit further comprises a plunger mounted on said chamber for movement into said chamber to expel fluid therefrom.

4. An apparatus as recited in claim 1 wherein said second end of said injection tube is formed with an orifice, the cross sectional area of said orifice being less than the cross sectional area of said lumen, to increase the velocity of the fluid when the fluid is expelled through the orifice.

5. An apparatus as recited in claim 4 wherein said orifice is generally circular with a diameter of about 0.008 inches.

6. An apparatus as recited in claim 4 wherein said second end of said injection tube is formed with a syringe tip around said orifice, said syringe tip being tapered to generally form a point around said orifice, to facilitate creating a seal between the skin area and said orifice.

7. An apparatus as recited in claim 1 wherein said drive mechanism comprises:
    a housing;
    a push rod slidably disposed on said housing;
    an impulse spring disposed on said housing for accelerating said push rod; and
    a perfusion spring disposed on said housing for moving said push rod.

8. An apparatus as recited in claim 7 wherein said impulse spring and said perfusion spring are mounted coaxially.

9. An apparatus as recited in claim 3 wherein said drive mechanism comprises:
    a housing;
    a push rod slidably disposed on said housing;
    an impulse spring disposed on said housing for accelerating said push rod; and
    a perfusion spring disposed on said housing for moving said push rod,
    and wherein said syringe unit is engageable with said drive mechanism to position said push rod longitudinally co-linear with said plunger, for said push rod to push said plunger to cause the fluid to be expelled from said aperture of said chamber.

10. An apparatus as recited in claim 9 wherein said impulse stage has a beginning and wherein said push rod collides with said plunger at said beginning of said impulse stage, and wherein said push rod urges against said plunger during said perfusion stage.

11. An apparatus as recited in claim 7 further comprising:
    a latch mounted on said housing for holding said push rod with said impulse spring in a compressed configuration and with said perfusion spring in a compressed configuration; and
    a trigger mounted on said housing for releasing said push rod from said latch to allow said push rod to be moved by said impulse spring and said perfusion spring.

12. An apparatus for injecting a fluid medicament through a skin area into a patient, which comprises:
- a chamber for containing the fluid, said chamber having an aperture;
- a plunger mounted on said chamber for movement into said chamber to expel the fluid through said aperture;
- actuator means for exerting forces on said plunger to expel the fluid from said chamber through said aperture and to sequentially puncture the skin area of the patient to create a hole therethrough and to cause the fluid to infuse into the patient through the hole;
- a suction compartment attached to said chamber, said suction compartment having an opening surrounding said aperture, said suction compartment having a suction port; and
- a vacuum source attachable in fluid communication with said suction port for establishing a partial vacuum in said suction compartment, to pull the skin area against said aperture and into said suction compartment to create a subcutaneous pocket for infusion of said fluid medicament.

13. An apparatus as recited in claim 12 wherein said actuator means is a drive mechanism comprising:
- a housing;
- a push rod slidably disposed on said housing;
- an impulse spring disposed on said housing for accelerating said push rod, said accelerated push rod colliding with said plunger and pushing said plunger with a first force to expel the fluid from said chamber through said aperture to create said hole through the skin area; and
- a perfusion spring disposed on said housing for pushing said plunger with a second force, said second force causing the fluid to be expelled from said chamber through said aperture to infuse into the patient through said hole in the skin area.

14. An apparatus as recited in claim 13 wherein said first force is greater than said second force, and wherein the duration of said first force is less than about 0.005 second, and wherein the duration of said second force is at least about 2 seconds.

15. A method for injecting a fluid medicament through a skin area into a patient, which comprises the steps of:
- providing a syringe unit, said syringe unit being formed with a chamber having an aperture, said chamber for containing the fluid and wherein said syringe unit further comprises a suction compartment having an opening surrounding said aperture, and wherein said suction compartment is formed with a suction port;
- providing a drive mechanism for selectively exerting forces on the fluid in said chamber to sequentially expel the fluid through said aperture in two stages, said stages being an impulse stage characterized by a first force wherein the fluid punctures the skin area of the patient to create a hole through the skin area, and a perfusion stage characterized by a second force wherein the fluid is injected into the patient through said hole, said second force being less than said first force;
- cocking said drive mechanism;
- placing the fluid in said chamber;
- engaging said syringe unit with said drive mechanism;
- positioning said aperture against the skin area of the patient;
- connecting a vacuum source in fluid communication with said port in said suction compartment, for creating a partial vacuum in said suction compartment when said opening of said suction compartment is placed against the skin area of the patient to pull the skin area against said aperture and to create a subcutaneous pocket for infusion of said fluid; and
- activating said drive mechanism to cause the fluid to be expelled through said aperture in said two stages.

16. A method as recited in claim 15 in which said impulse stage has a duration of less than about 0.005 second, and said perfusion stage has a duration of at least about 2 seconds.

* * * * *